(12) United States Patent
Luo

(10) Patent No.: US 11,986,580 B2
(45) Date of Patent: May 21, 2024

(54) WEARABLE BREAST PUMP

(71) Applicant: Guangzhou Talong Technology Co., Ltd., Guangzhou (CN)

(72) Inventor: Likang Luo, Guangzhou (CN)

(73) Assignee: GUANGZHOU TALONG TECHNOLOGY CO., LTD., Guangzhou (CN)

( * ) Notice: Subject to any disclaimer, the term of this patent is extended or adjusted under 35 U.S.C. 154(b) by 0 days.

(21) Appl. No.: 18/348,368

(22) Filed: Jul. 7, 2023

(65) Prior Publication Data
US 2023/0347026 A1 Nov. 2, 2023

(30) Foreign Application Priority Data

Jun. 6, 2023 (CN) .......................... 202310668789.7

(51) Int. Cl.
*A61M 1/06* (2006.01)
(52) U.S. Cl.
CPC .............. *A61M 1/069* (2021.05); *A61M 1/06* (2013.01); *A61M 1/067* (2021.05)
(58) Field of Classification Search
CPC ...... A61M 1/067; A61M 1/069; A61M 1/062; A61M 1/06
See application file for complete search history.

(56) References Cited

U.S. PATENT DOCUMENTS

| 11,554,198 B1 * | 1/2023 | Pan ........................ A61M 1/062 |
| 11,712,500 B1 * | 8/2023 | Wang ...................... A61M 1/82 604/74 |
| 2013/0072866 A1 | 3/2013 | Hegen |
| 2014/0052057 A1 | 2/2014 | Darnell et al. |
| 2017/0182231 A1 | 6/2017 | Aalders et al. |
| 2018/0008758 A1 * | 1/2018 | Garbez ................... A61M 1/066 |
| 2021/0093761 A1 * | 4/2021 | Hwang ................... A61M 39/22 |
| 2022/0111128 A1 * | 4/2022 | Visconti ................. A61M 1/067 |
| 2023/0123294 A1 * | 4/2023 | Chang ............... A61M 1/06935 604/74 |
| 2023/0211054 A1 * | 7/2023 | Mou ........................ A61M 1/06 604/74 |
| 2023/0211055 A1 * | 7/2023 | Mou .................... A61M 1/0697 604/74 |

FOREIGN PATENT DOCUMENTS

| CN | 114767972 A | * | 7/2022 | |
| CN | 115192800 A | * | 10/2022 | ............ A61M 1/067 |

* cited by examiner

*Primary Examiner* — Jenna Zhang
(74) *Attorney, Agent, or Firm* — Zhigang Ma

(57) ABSTRACT

The present disclosure provides a wearable breast pump, including a host machine, a cup and a flowing channel unit. The host machine includes a variable pressure chamber. The cup is detachably connected to the host machine through the variable pressure chamber. The flowing channel unit is detachably arranged inside the cup and separates an internal space of the cup into a flowing channel and a milk storage bowl. The flowing channel is communicated with the variable pressure chamber, the milk storage bowl and the outside. The wearable breast pump has the flowing channel unit arranged inside the cup, achieving structural optimization, whereby making the structure more concise and the shape more beautiful, as well as increasing the integration level and reducing the occupied space.

8 Claims, 7 Drawing Sheets

WEARABLE BREAST PUMP

TECHNICAL FIELD

The present disclosure belongs to the technical field of breast milking equipment, more particularly to a wearable breast pump.

BACKGROUND

Breast pump refers to a tool used for squeezing out the milk accumulated in the breast, which is generally employed when an infant cannot directly suck on the breast, or when the mother's nipples are experiencing a problem, or when a working mother still hopes to breastfeed an infant.

Current breast pumps include a host machine, a milking structure and a milk bottle, which are independent of each other. During practical application, it is needed to flush the breast pump after milking. However, due to structure restriction, current breast pumps have to be demounted many times, increasing the labor of demounting.

SUMMARY

It is an object of the present disclosure to provide a wearable breast pump, to address the above problems in the existing technologies.

In order to achieve the above purpose, the present disclosure employs the following technical solution.

A wearable breast pump includes a host machine, a cup and a flowing channel unit. The host machine includes a variable pressure chamber. The cup is detachably connected to the host machine through the variable pressure chamber. The flowing channel unit is detachably arranged inside the cup and separates an internal space of the cup into a flowing channel and a milk storage bowl. The flowing channel is communicated with the variable pressure chamber, the milk storage bowl and the outside.

In one possible design, the host machine includes a housing, a control module and an air pump module. The housing is open at one end and has the variable pressure chamber provided at the open end. The control module and the air pump module are both arranged inside the housing. The control module is connected to the air pump module in a communication manner. The air pump module is connected to the variable pressure chamber and is connected to the flowing channel unit through the variable pressure chamber.

In one possible design, the variable pressure chamber includes a spacer, a chamber cover plate and a silicone suction cup.

The spacer is fixed at the open end of the housing and isolates the housing from the outside. The spacer is formed thereon with an air hole communicated with the air pump module. The chamber cover plate is connected to the spacer and is arranged opposite to the spacer. A variable pressure chamber body is enclosed between the spacer and the chamber cover plate.

The silicone suction cup is moveably arranged inside the variable pressure chamber body, and correspondingly, the chamber cover plate is formed thereon with an air hole unit directly opposite the silicone suction cup. The air hole unit is communicated with the outside.

In one possible design, the chamber cover plate includes an outer ring body and a cover plate body. The outer ring body has opposite upper opening and lower opening. The upper opening is connected to the housing and the lower opening is connected to the cover plate body. The silicone suction cup and the spacer are placed on an inner circumference of the outer ring body from bottom to top in turn, and a clamping groove is formed between the spacer and the outer ring body that fits with the silicone suction cup. An outer circumference of the outer ring body is configured to connect to the cup. Correspondingly, a bottom surface of the spacer is provided with a limit ring that is opposite to the outer ring body to form the clamping groove.

In one possible design, the air pump module includes an air pump, a valve body, a negative pressure tube and a positive pressure tube. The air pump and the valve body are each connected to the control module in a communication manner. The negative pressure tube is connected to the air pump and the variable pressure chamber. The positive pressure tube is connected to the valve body and the variable pressure chamber.

In one possible design, the flowing channel unit includes a three-way valve, a breast flange and a duckbill valve. The three-way valve is formed thereon with an air vent, a liquid inlet and a liquid outlet respectively. The three-way valve has the breast flange fixed thereon and is communicated with the breast flange through the air vent. The liquid outlet of the three-way valve is provided with the duckbill valve. The liquid inlet of the three-way valve is communicated with the outside.

In one possible design, the cup includes a cup body and a silicone trumpet cover.

The cup body has a first opening and a second opening. The first opening is configured to connect to the host machine, and the second opening is provided with the silicone trumpet cover. The silicone trumpet cover has opposite large-diameter end and smaller-diameter end. The large-diameter end is connected to the second opening. The smaller-diameter end extends toward an inside of the cup body and is connected to the flowing channel unit.

Correspondingly, the flowing channel unit is positioned inside the cup body. The flowing channel unit includes a three-way valve and a breast flange. A liquid inlet of the three-way valve is connected to the smaller-diameter end of the silicone trumpet cover. The three-way valve is provided thereon with the breast flange. The breast flange is connected to the first opening.

In one possible design, the cup body is formed thereon with an exhaust and liquid extraction port that is positioned on an upper part of the cup body and is adjacent to the host machine.

In one possible design, the first opening of the cup body is bent downward to form a clamping ring that is provided thereon with a clamping groove fitting with the variable pressure chamber. Correspondingly, an outer circumferential surface of the variable pressure chamber is provided thereon with a clamping surface fitting with the clamping groove.

The outer circumferential surface of the variable pressure chamber is further provided thereon with an upper abutting ring positioned on an inner side of the clamping surface. Correspondingly, the breast flange is provided thereon with a fit lower abutting ring. The upper abutting ring and the lower abutting ring can abut against each other.

In one possible design, one of the first opening and the large-diameter end is provided thereon with a hook plate, while the other one is formed thereon with a buckle groove. The hook plate can be buckled into the buckle groove to connect the cup body and the silicone trumpet cover. The smaller-diameter end is formed with an annular groove fitting with the flowing channel unit. One end of the flowing channel unit is inserted into the annular groove, while the other end of the flowing channel unit abuts against the cup body.

It is easy to understand that the three-way valve in the flowing channel unit is configured to connect to the silicone trumpet cover, hence the liquid inlet of three-way valve is constructed as an annular structure fitting with the annular groove.

The present disclosure has the following beneficial effects.

The wearable breast pump has the flowing channel unit arranged inside the cup, achieving structural optimization, whereby making the structure more concise and the shape more beautiful, as well as increasing the integration level and reducing the occupied space. The host machine is detachably connected to the cup, facilitating convenient demounting and cleaning, reducing the labor of reinstalling after demounting and cleaning, and improving the convenience of usage The wearable breast pump has the structure simplified and integrated, which can better adhere to the human body, with better wearing performance and higher convenience.

DETAILED DESCRIPTION OF THE EMBODIMENTS

Figure 1:
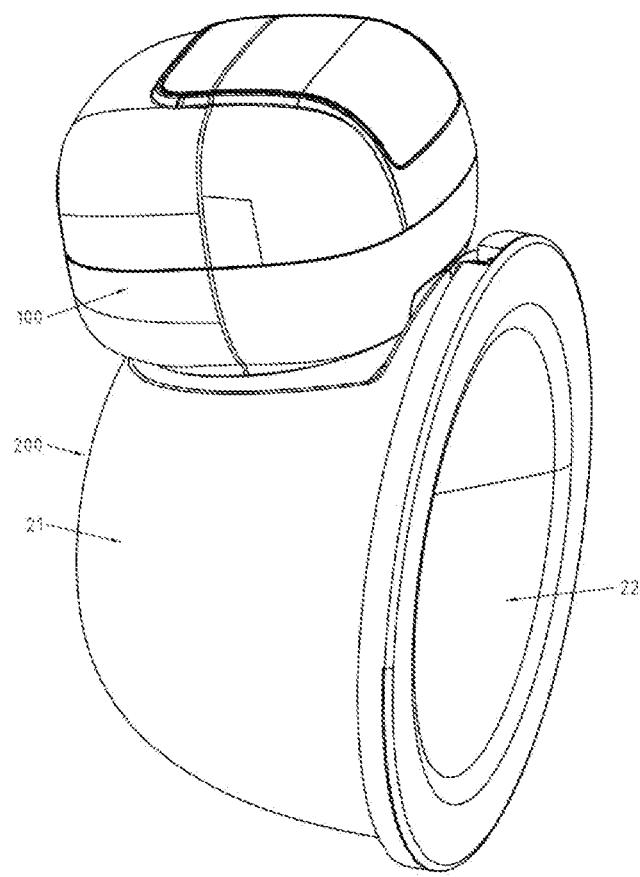
FIG. 1 is a structure diagram of a wearable breast pump.
Figure 2:
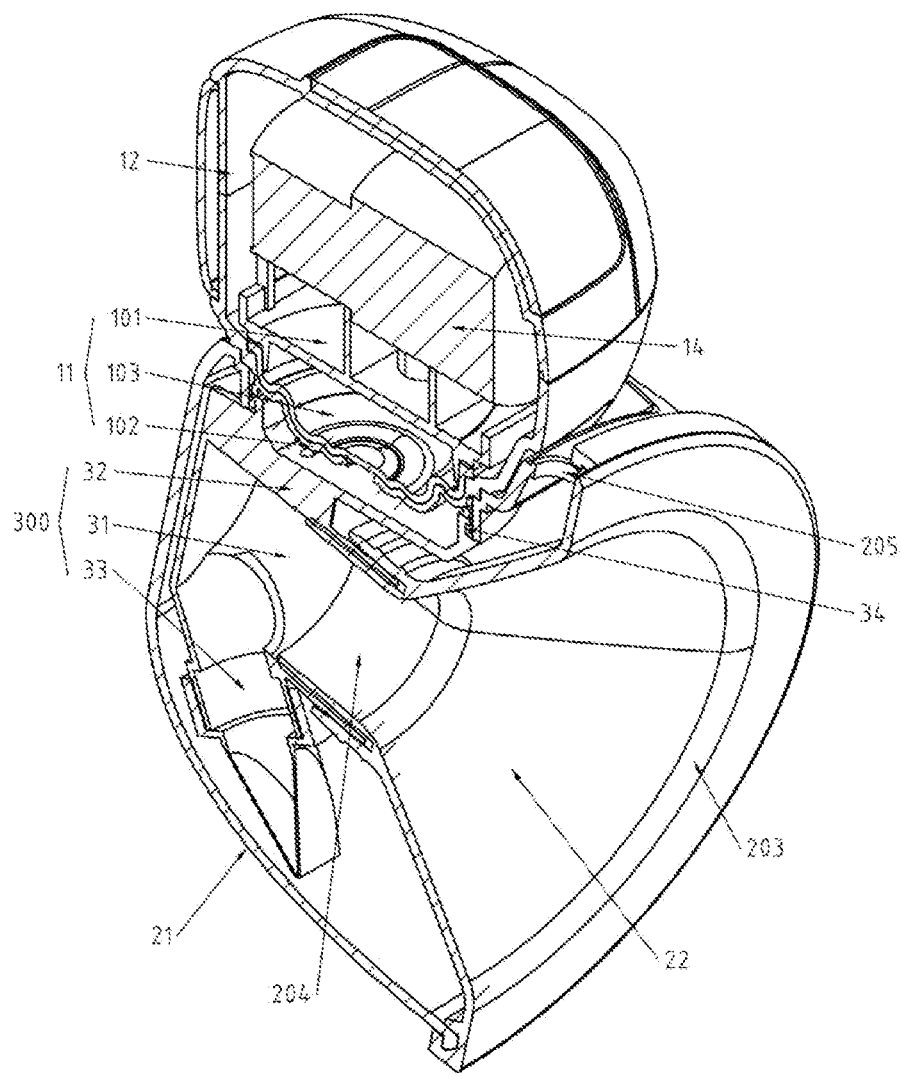
FIG. 2 is a structure diagram of a first cross section of FIG. 1.
Figure 3:
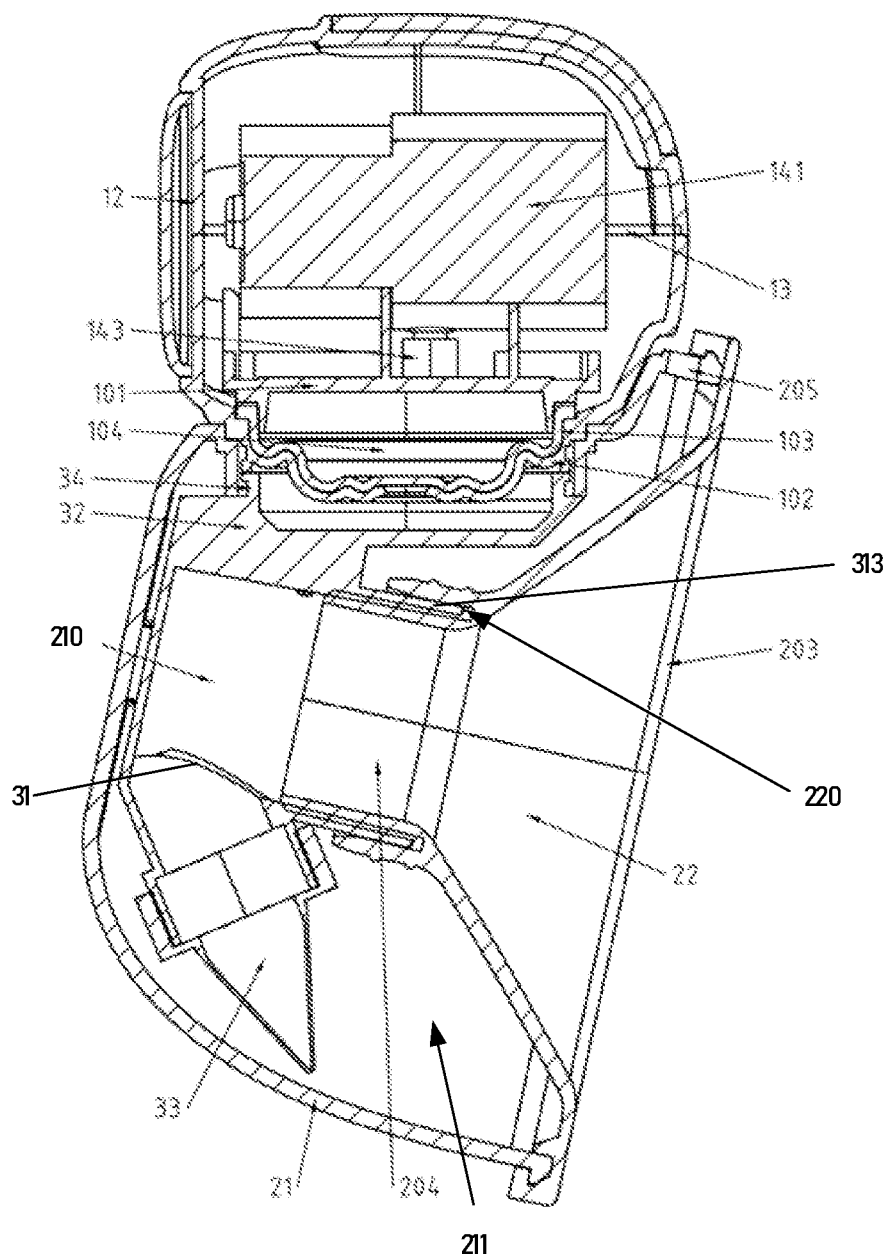
FIG. 3 is an isometric structure diagram of FIG. 2.
Figure 4:
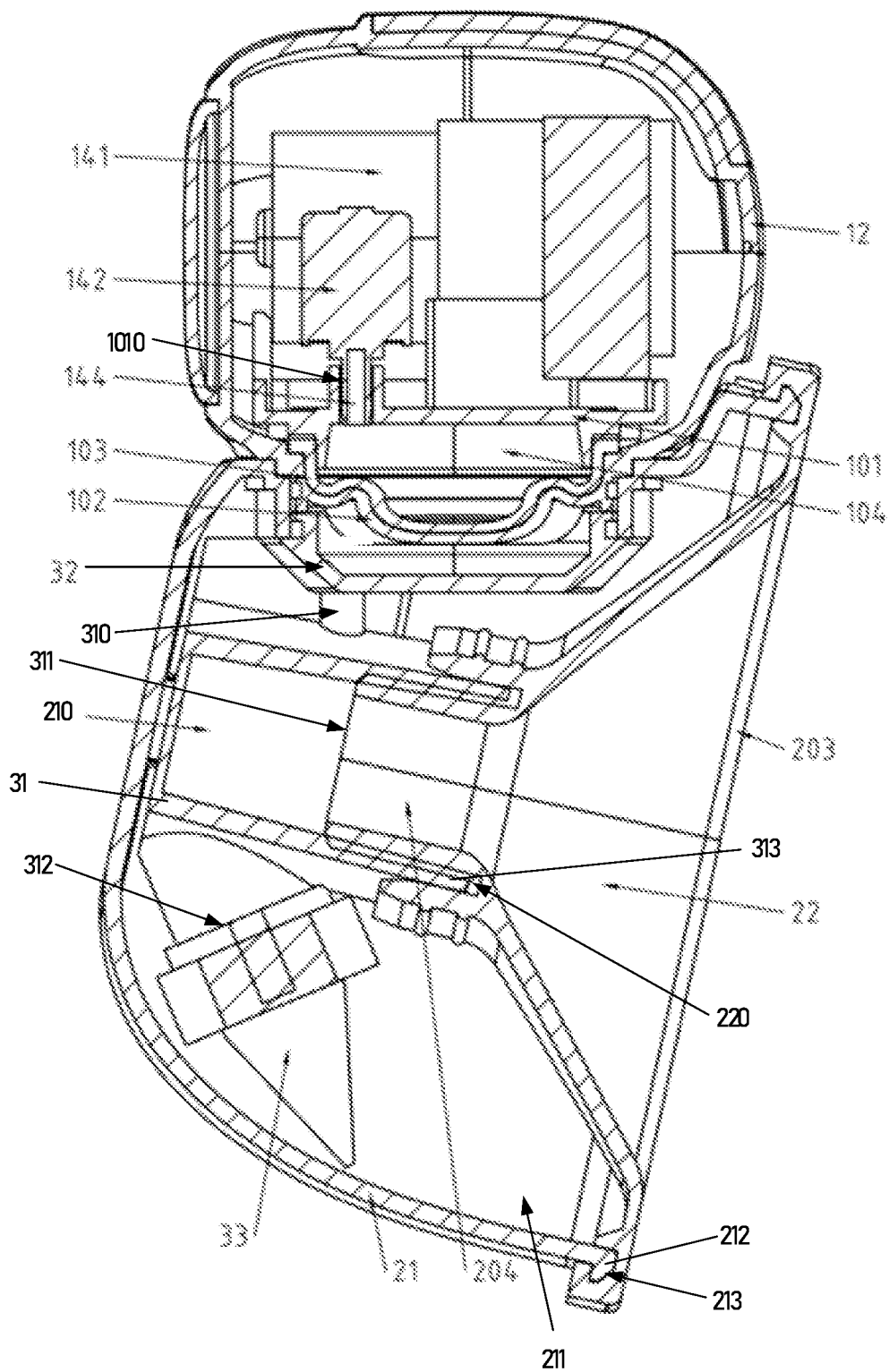
FIG. 4 is a structure diagram of a second cross section of FIG. 1.

For a better understanding of the technical solution in the embodiments of the present disclosure or in the prior art, the present disclosure will be briefly introduced below in combination with the drawings and embodiments or the description of the prior art. Apparently, the descriptions on the drawings of structures below are merely some embodiments of the present disclosure. For the ordinary skill in the field, other drawings may be obtained according to these drawings without creative effort. It should be noted here that the description of these embodiments is merely to help understand the present disclosure, rather than to limit the present disclosure.

EMBODIMENTS

As shown in FIG. 1 to FIG. 7, a wearable breast pump includes a host machine 100, a cup 200 and a flowing channel unit 300. The host machine 100 incudes a variable pressure chamber 11. The cup 200 is detachably connected to the host machine 100 through the variable pressure chamber 11. The flowing channel unit 300 is detachably arranged inside the cup 200 and separates an internal space of the cup 200 into a flowing channel 210 and a milk storage bowl 211. The flowing channel 210 is communicated with the variable pressure chamber 11, the milk storage bowl and the outside.

Herein, when in use, the wearable breast pump simulates a sucking action to stimulate a breast and initiates milk let-down, allowing the milk stored in breast acini to release through lactiferous ducts. For the released milk, the wearable breast pump simulates the sucking action and generates a negative pressure by which the milk is sucked into the flowing channel and finally stored in the milk storage bowl.

In the above process, the host machine 100 drives the variable pressure chamber 11 to form a negative pressure-positive pressure-negative pressure cycle. The change of pressure is transmitted to a human breast through the flowing channel and the cup 200, simulating the sucking action and stimulating the breast. For the milk flowing into the flowing channel, the positive pressure is recovered and the milk is driven into the milk storage bowl from the flowing channel. The cup 200 on one hand is configured to store the milk, and on the other hand can cover the breast. Through the breast, the flowing channel unit 300 is sealed, forming a relatively enclosed space, whereby to improve the efficiency of milking of the host machine 100. Meanwhile, the cup 200 also guides the milk into the flowing channel unit 300 to flow along the flowing channel. The flowing channel unit 300 is hidden inside the cup 200, relatively reducing the volume of the milk storage bowl, but then making the structure more concise and the shape more beautiful, as well as increasing the integration level and reducing the occupied space.

During work, the cup 200 covers a breast, the host machine 100 is started, and the variable pressure chamber 11 forms a negative pressure-positive pressure-negative pressure cycle. The cup 200 combines with the pressure circulation to simulate a sucking action, initiating milk let-down and enabling the milk to flow out. When the variable pressure chamber 11 is at a negative pressure, a sucking force is generated, and the milk is sucked out to flow into the flowing channel. When the variable pressure chamber 11 is at a positive pressure, a push force is generated to push the milk, whereby the milk storage bowl is opened to store the milk. The cycle is repeated, until the milk is completely sucked out. Then, the host machine 100 is shut down, and the wearable breast pump is removed off to flush.

Compared with the existing technologies, the wearable breast pump has the flowing channel unit 300 arranged inside the cup 200, achieving structural optimization, whereby making the structure more concise and the shape more beautiful, as well as increasing the integration level and reducing the occupied space. The host machine 100 is detachably connected to the cup 200, facilitating convenient demounting and cleaning, reducing the labor of reinstalling after demounting and cleaning, and improving the convenience of usage.

In the present embodiment, the host machine 100 includes a housing 12, a control module 13 and an air pump module 14. The housing 12 is open at one end and has the variable pressure chamber 11 provided at the open end. The control module 13 and the air pump module 14 are both arranged inside the housing 12. The control module 13 is connected to the air pump module 14 in a communication manner. The air pump module 14 is connected to the variable pressure chamber 11 and is connected to the flowing channel unit 300 through the variable pressure chamber 11.

Based on the above design scheme, the housing 12 can be constructed as any appropriate shape, to meet the requirements of different users. The control module 13 on one hand receives a command from a user, and on the other hand transmits the command to the air pump module 14, so that the air pump module 14 generates a corresponding action. It is easy to understand that the control module 13 is inbuilt with multiple work modes, including, but not limited to, a massage mode and a milking mode, and meanwhile can control respective frequencies of the massage mode and the milking mode. The work mode and the work frequency combine with each other to form diverse work states, to meet the requirements of users. The air pump module 14 combines with the variable pressure chamber 11 to form the pressure cycle.

For the variable pressure chamber 11, in order to improve the working effect of the pressure cycle, it is necessary to improve the tightness. Since the flowing channel is communicated with the variable pressure chamber 11, the milk storage bowl and the outside, sealing the open end of the housing 12 by means of the variable pressure chamber 11 not only improves the tightness, but also reduces the probability that the milk flows into the housing 12 to impact the operation of each part inside the housing 12. Meanwhile, when the wearable breast pump is in use, the cup 200 covers the breast and seals the breast off the outside, whereby the flowing channel is intercommunicated with the milk storage bowl only, ensuring the milk to flow into the milk storage bowl.

The control module 13 can select any appropriate model available on the market. Meanwhile, the control module 13 can be connected to a terminal in a communication manner, so that a user controls the operation of the wearable breast pump through the terminal. Alternatively, as shown in FIG. 1, the control module 13 further includes a touch pad embedded on the housing 12, so that a user controls the operation of the wearable breast pump through the touch pad.

Optionally, inside the housing 12 is provided a power supply module that is electrically connected to the control module 13 and the air pump module 14 and supplies power to the control module 13 and the air pump module 14. In consideration of the sealed structure of the housing 12, the power supply module preferably selects a rechargeable battery. Correspondingly, the housing 12 is formed thereon with a charging interface electrically connected to the power supply module.

In the present embodiment, the variable pressure chamber 11 includes a spacer 101, a chamber cover plate 102 and a silicone suction cup 103.

The spacer 101 is fixed at the open end of the housing 12 and isolates the housing 12 from the outside. The spacer 101 is formed thereon with an air hole 1010 communicated with the air pump module 14. The chamber cover plate 102 is connected to the spacer 101 and is arranged opposite to the spacer 101. A variable pressure chamber body 104 is enclosed between the spacer 101 and the chamber cover plate 102.

The silicone suction cup 103 is moveably arranged inside the variable pressure chamber body 104, and correspondingly, the chamber cover plate 102 is formed thereon with an air hole unit 105 directly opposite the silicone suction cup 103. The air hole unit 105 is communicated with the outside.

Based on the above design scheme, a cavity is formed between the spacer 101 and the chamber cover plate 102, that is, the variable pressure chamber body 104. The silicone suction cup 103 is moveably arranged inside the variable pressure chamber body 104. The spacer 101 is formed thereon with the air hole 1010 communicated with the air pump module 14. The air pump module 14 sends air into and out of an inside of the variable pressure chamber body 104, whereby driving the silicone suction cup 103 to reciprocate inside the variable pressure chamber body 104. The activity of the silicone suction cup 103 is transmitted to the flowing channel to cause a cyclic change of pressure inside the flowing channel, that is, the pressure cycle. In addition, the application of the silicone suction cup 103 enables a more uniform change of pressure inside the flowing channel, not only improving the working effect of the wearable breast pump, but also being conducive to protecting the breast.

Correspondingly, the chamber cover plate 102 is formed thereon with an air hole unit 105 to interconnect the variable pressure chamber body 104 and the flowing channel, enabling the flowing of gas. Meanwhile, the wearable breast pump needs to be cleaned after usage. For the host machine 100, the chamber cover plate 102 protects the silicone suction cup 103, whereby reducing the damage of flushing to the silicone suction cup 103 and improving the working effect and service life of the silicone suction cup 103.

Figure 5:
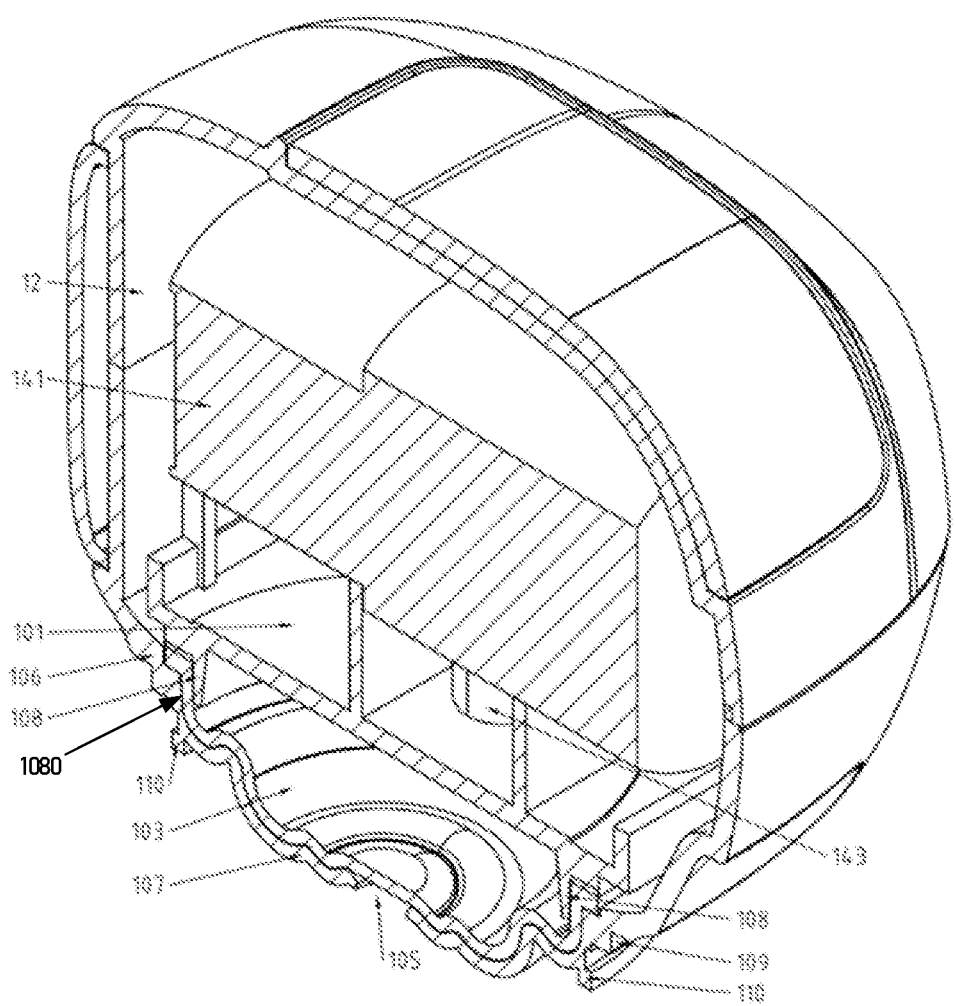
FIG. 5 is a sectional structure diagram of a host machine.
Figure 6:
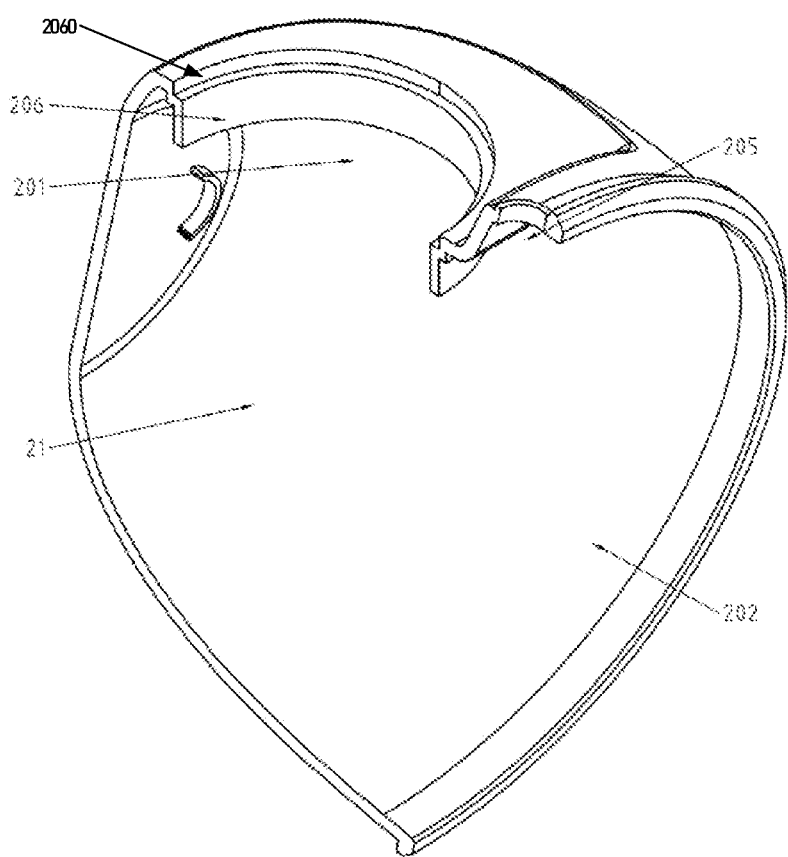
FIG. 6 is a structure diagram of a cup body.
Figure 7:
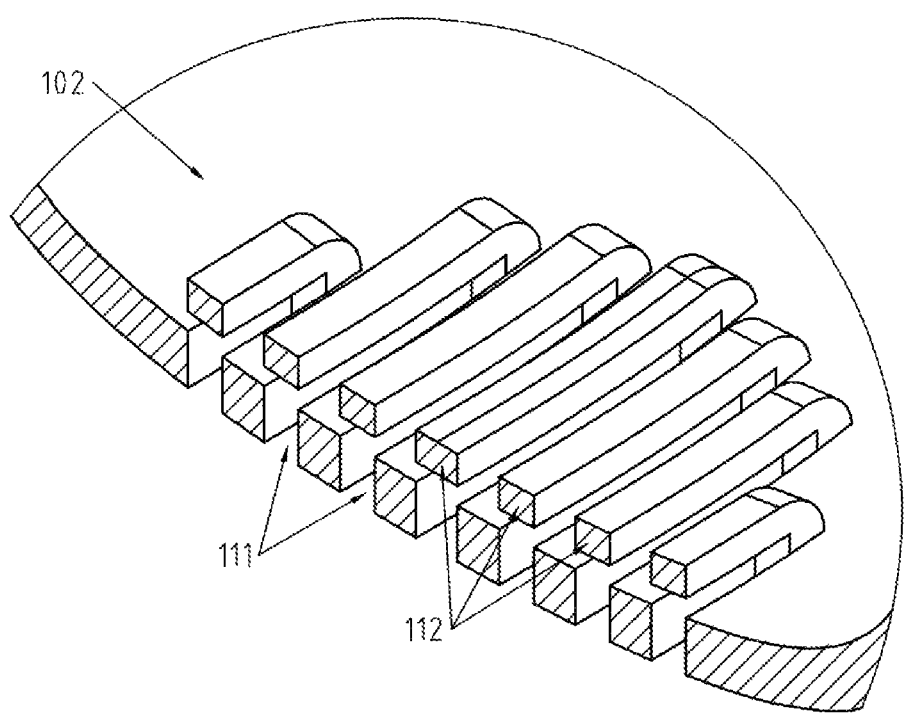
FIG. 7 is a structure diagram of an air hole unit.
In the drawings:
100, a host machine; 11, a variable pressure chamber; 12, a housing; 13, a control module; 14, an air pump module; 101, a spacer; 102, a chamber cover plate; 103, a silicone suction cup; 104, a variable pressure chamber body; 105, an air hole unit; 106, an outer ring body; 107, a cover plate body; 108, a limit ring; 109, a clamping surface; 110, an upper abutting ring; 111, a ventilation slot; 112, a baffle bar; 141, an air pump; 142, a valve body; 143, a negative pressure tube; 144, a positive pressure tube; 200, a cup; 21, a cup body; 22, a silicone trumpet cover; 201, a first opening; 202, a second opening; 203, a large-diameter end; 204, a smaller-diameter end; 205, an exhaust and liquid extraction port; 206, a clamping ring; 300, a flowing channel unit; 31, a three-way valve; 32, a breast flange; 33, a duckbill valve; and 34, a lower abutting ring.

Optionally, the air hole unit 105 is constructed as a ventilation hole. As shown in FIG. 5, there is at least one ventilation hole formed. Alternatively, as shown in FIG. 7, the air hole unit 105 includes ventilation slots 111 and baffle bars 112. A plurality of ventilation slots 111 are formed that are distributed on the chamber cover plate 102 at equal intervals. Correspondingly, a plurality of baffle bars 112 are arranged that are distributed between the ventilation slots 111 and the silicone suction cup 103 at equal intervals. Correspondingly, the ventilation slots 111 and the baffle bars 112 are in one-to-one correspondence. Based on the above design scheme, the baffle bars 112 form a height difference to abut against the silicone suction cup 103, whereby reducing the downward movement range of the silicone suction cup 103 and thus protecting the silicone suction cup 103, so that the silicone suction cup 103 can remain a good elasticity.

As shown in FIG. 5, the chamber cover plate 102 includes an outer ring body 106 and a cover plate body 107. The outer ring body 106 has opposite upper opening and lower opening. The upper opening is connected to the housing 12 and the lower opening is connected to the cover plate body 107. The silicone suction cup 103 and the spacer 101 are placed on an inner circumference of the outer ring body 106 from bottom to top in turn, and a clamping groove 1080 is formed between the spacer 101 and the outer ring body 106 that fits with the silicone suction cup 103. An outer circumference of the outer ring body 106 is configured to connect to the cup 200. Correspondingly, a bottom surface of the spacer 101 is provided with a limit ring 108 that is opposite to the outer ring body 106 to form the clamping groove 1080.

Based on the above design scheme, connection is achieved through the chamber cover plate 102, the outer ring body 106 is connected to the housing 12 to form a relatively enclosed space, reducing the contact of each part of the housing 12 with the outside, avoiding the milk entering the housing 12 through a gap between the outer ring body 106 and the silicone suction cup 103 during the milking process, and ensuring the normal operation of each part inside the housing 12. Meanwhile, the spacer 101 is depressed to form a clamping groove and apply a clamping force, which on one hand achieves the connection between the spacer 101, the silicone suction cup 103 and the chamber cover plate 102, and on the other hand improves the tightness of connection and the anti-permeation capability.

In the present embodiment, the air pump module 14 includes an air pump 141, a valve body 142, a negative pressure tube 143 and a positive pressure tube 144. The air pump 141 and the valve body 142 are each connected to the control module 13 in a communication manner. The negative pressure tube 143 is connected to the air pump 141 and the variable pressure chamber 11. The positive pressure tube 144 is connected to the valve body 142 and the variable pressure chamber 11.

Based on the above design scheme, the air pump 141 is communicated with the variable pressure chamber body 104 through the negative pressure tube 143, and the air pump 141 sucks in air after being started, whereby to cause the silicone suction cup 103 to move upwardly and form a negative pressure. The silicone suction cup 103 moves to an upper limit position, the valve body 142 is turned on, and external air flows into the variable pressure chamber body 104 via the positive pressure tube 144, forming a positive pressure and driving the silicone suction cup 103 to move downwardly. The silicone suction cup 103 moves to a lower limit position, then the valve body 142 is turned off, and the air pump 141 sucks in air again, achieving a reciprocation of the silicone suction cup 103, hence achieving the pressure cycle.

It is understandable that the air pump 141 is connected to the control module 13 in a communication manner, and the air pump 141 can select any model available on the market. The valve body 142 preferably selects a solenoid valve, and the solenoid valve is connected to the control module 13 in a communication manner. The negative pressure tube 143 and the positive pressure tube 144 select any appropriate models available on the market respectively.

In the present embodiment, the flowing channel unit 300 includes a three-way valve 31, a breast flange 32 and a duckbill valve 33. The three-way valve 31 is formed thereon with an air vent 310, a liquid inlet 311 and a liquid outlet 312 respectively. The three-way valve 31 has the breast flange 32 fixed thereon and is communicated with the breast flange 32 through the air vent 310. The liquid outlet of the three-way valve 31 is provided with the duckbill valve 33. The liquid inlet of the three-way valve 31 is communicated with the outside.

Based on the above design scheme, the three-way valve 31 is connected to the variable pressure chamber 11 through the breast flange 32, and the breast flange 32 is detachably connected to the variable pressure chamber 11, so that it can be detached to flush after milking. Meanwhile, a cavity is formed between the breast flange 32 and the variable pressure chamber 11, and the cavity is communicated with the three-way valve 31 through the air vent. The variable pressure chamber 11, the cavity, the air vent and the three-way valve 31 form an intercommunicated air path, then the change of pressure inside the variable pressure chamber 11 will be transmitted to the three-way valve 31. The duckbill valve 33 is one type of one-way valve, that is, when the milk is pushed by a positive pressure, the duckbill valve 33 is turned on, so that the milk flows into the milk storage bowl from the flowing channel. The duckbill valve 33 is turned off at a negative pressure or normal pressure, preventing the milk inside the milk storage bowl from flowing out, hence reducing the possibility of leakage of milk.

In the present embodiment, the cup 200 includes a cup body 21 and a silicone trumpet cover 22.

The cup body 21 has a first opening 201 and a second opening 202. The first opening 201 is configured to connect to the host machine 100, and the second opening 202 is provided with the silicone trumpet cover 22. The silicone trumpet cover 22 has opposite large-diameter end 203 and smaller-diameter end 204. The large-diameter end 203 is connected to the second opening 202. The smaller-diameter end 204 extends toward an inside of the cup body 21 and is connected to the flowing channel unit 300.

Correspondingly, the flowing channel unit 300 is positioned inside the cup body 21. The flowing channel unit 300 includes a three-way valve 31 and a breast flange 32. A liquid inlet of the three-way valve 31 is connected to the smaller-diameter end 204 of the silicone trumpet cover 22. The three-way valve 31 is provided thereon with the breast flange 32; and the breast flange 32 is connected to the first opening 201.

Based on the above design scheme, the cup body 21 can be constructed as any appropriate shape, as long as a certain space can be enclosed. The variable pressure chamber 11 is fixed on the first opening 201, and the silicone trumpet cover 22 is buckled on the second opening 202. Meanwhile, the flowing channel unit 300 is positioned inside the cup body 21. Therefore, the flowing channel unit 300 should be placed inside the cup body 21 before the silicone trumpet cover 22 is buckled. The flowing channel unit 300 is connected to the variable pressure chamber 11 to achieve preliminary fixation. In view of the above, the variable pressure chamber 11 and the silicone trumpet cover 22 can achieve a sealing effect to isolate the milk storage bowl from the outside.

An outer circumferential surface of the silicone trumpet cover 22 is covered inside the cup body 21 to seal the cup body 21. An inner circumferential surface of the silicone trumpet cover 22 is constructed as a curved surface fitting with the curve of the breast, achieving a better fitness to improve the stimulating effect on the breast. Meanwhile, the silicone trumpet cover 22 selects silicone having certain elasticity, which can stimulate or massage the breast under the action of the pressure cycle. Therefore, besides the milking function, the wearable breast pump can also be used for massaging the breast, achieving function expansion.

In one possible implementation, the cup body 21 is formed thereon with an exhaust and liquid extraction port 205 that is positioned on an upper part of the cup body 21 and is adjacent to the host machine 100. Based on the above design scheme, when the milk flows into the milk storage bowl, the air inside the milk storage bowl is exhausted through the exhaust and liquid extraction port 205, ensuring the milk to successfully flow into the milk storage bowl. The milk stored in the milk storage bowl can also be poured out through the exhaust and liquid extraction port 205, for subsequent usage. Meanwhile, the exhaust and liquid extraction port 205 is positioned on the upper part of the cup body 21 and is adjacent to the host machine 100. Relatively, the exhaust and liquid extraction port 205 is positioned above, whereby reducing the risk of leakage of milk.

In one possible design, the first opening 201 of the cup body 21 is bent downward to form a clamping ring 206 that is provided thereon with a clamping recess 2060 fitting with the variable pressure chamber 11. Correspondingly, an outer circumferential surface of the variable pressure chamber 11 is provided thereon with a clamping surface 109 fitting with the clamping recess 2060. Based on the above design scheme, the cup body 21 is connected to the host machine 100 through clamping, whereby to facilitate repeated demounting and flushing to avoid residues and improve the hygiene of the wearable breast pump. Optionally, as shown in FIG. 2, FIG. 3, FIG. 4 and FIG. 6, the clamping surface 109 is positioned on a circumferential surface of the outer ring body 106.

Optionally, at least one of the clamping recess 2060 and the clamping surface 109 is provided with a detachable flexible layer, whereby the contact area is increased by deformation and the absolute value of the clamping force is improved. Meanwhile, in consideration of the abrasion due to long-term usage that could result in degradation of clamping performances, the flexible layer is constructed to be detachable, for timely replacement.

In one possible design, the outer circumferential surface of the variable pressure chamber 11 is further provided thereon with an upper abutting ring 110 positioned on an inner side of the clamping surface 109. Correspondingly, the breast flange 32 is provided thereon with a fit lower abutting ring 34. The upper abutting ring 110 and the lower abutting ring 34 can abut against each other. In view of the above, when the host machine 100 is connected to the cup 200, the upper abutting ring 110 and the lower abutting ring 34 abut against each other to form an enclosed structure, whereby to improve the tightness at the connection between the host machine 100 and the cup 200 and avoid the leakage of milk.

Preferably, as shown in FIG. 2, FIG. 3, FIG. 4 and FIG. 6, the upper abutting ring 110 is positioned on the outer circumferential surface of the outer ring body 106, and the upper abutting ring 110 is coaxial with the clamping surface 109 and positioned on the inner side of the clamping surface 109.

For the connection of the silicone trumpet cover, the present embodiment provides a practically feasible connection scheme. As shown in FIG. 2, FIG. 3, FIG. 4 and FIG. 6, one of the second opening 202 and the large-diameter end 203 is provided thereon with a hook plate 212, while the other one is formed thereon with a buckle groove 213. The hook plate can be buckled into the buckle groove to connect the cup body 21 and the silicone trumpet cover 22. The smaller-diameter end 204 is formed with an annular groove fitting with the flowing channel unit 300. One end of the flowing channel unit 300 is inserted into the annular groove 220, while the other end of the flowing channel unit 300 abuts against the cup body 21.

It is easy to understand that the three-way valve 31 in the flowing channel unit 300 is configured to connect to the silicone trumpet cover 22, hence the liquid inlet of three-way valve 31 is constructed as an annular structure 313 fitting with the annular groove 220.

Finally, it should be noted that the above are preferred embodiments of the present disclosure merely and are not intended to limit scope of protection of the present disclosure. Any modifications, equivalent substitutions and improvements, etc., made within the spirit and principle of the present disclosure are all intended to be included in the scope of protection of the present disclosure.

What is claimed is:

1. A wearable breast pump, comprising a host machine (100), a cup (200) and a flowing channel unit (300), the host machine (100) comprising a variable pressure chamber (11), the cup (200) being detachably connected to the host machine (100) through the variable pressure chamber (11), the flowing channel unit (300) being detachably arranged inside the cup (200) and separating an internal space of the cup (200) into a flowing channel (210) and a milk storage bowl (211), and the flowing channel (210) being communicated with the variable pressure chamber (11), the milk storage bowl (211), and the outside of the wearable breast pump;
wherein the cup (200) comprises a cup body (21) and a silicone trumpet cover (22);
the cup body (21) has a first opening (201) and a second opening (202); the first opening (201) is configured to connect to the host machine (100), and the second opening (202) is provided with the silicone trumpet cover (22); the silicone trumpet cover (22) has a larger-diameter end (203) opposite a smaller-diameter end (204); the large-diameter end (203) is connected to the second opening (202); and the smaller-diameter end (204) extends toward an inside of the cup body (21) and is connected to the flowing channel unit (300); and
correspondingly, the flowing channel unit (300) is positioned inside the cup body (21); the flowing channel unit (300) comprises a three-way valve (31) and a breast flange (32); a liquid inlet (311) of the three-way valve (31) is connected to the smaller-diameter end (204) of the silicone trumpet cover (22); the three-way valve (31) is provided thereon with the breast flange (32); and the breast flange (32) is connected to the first opening (201);
wherein the variable pressure chamber (11) comprises a spacer (101), a chamber cover plate (102) and a silicone suction cup (103);
the spacer (101) is fixed at the open end of the housing (12) and isolates the housing (12) from the outside of the variable pressure chamber; the spacer (101) is formed thereon with an air hole (1010) communicated with the air pump module (14); the chamber cover plate (102) is connected to the spacer (101) and is arranged opposite to the spacer (101); and a variable pressure chamber body (104) is enclosed between the spacer (101) and the chamber cover plate (102); and
the silicone suction cup (103) is moveably arranged inside the variable pressure chamber body (104), and correspondingly, the chamber cover plate (102) is formed thereon with an air hole unit (105) directly opposite the silicone suction cup (103), and the air hole unit (105) is communicated with the outside of the variable pressure chamber.

2. The wearable breast pump according to claim 1, wherein the host machine (100) comprises a housing (12), a control module (13) and an air pump module (14); the housing (12) is open at one end and has the variable pressure chamber (11) provided at the open end; the control module (13) and the air pump module (14) are both arranged inside the housing (12); the control module (13) is connected to the air pump module (14) in a communication manner; and the air pump module (14) is connected to the variable pressure chamber (11) and is connected to the flowing channel unit (300) through the variable pressure chamber (11).

3. The wearable breast pump according to claim 2, wherein the air pump module (14) comprises an air pump (141), a valve body (142), a negative pressure tube (143) and a positive pressure tube (144); the air pump (141) and the valve body (142) are each connected to the control module (13) in a communication manner; the negative pressure tube (143) is connected to the air pump (141) and the variable pressure chamber (11); and the positive pressure tube (144) is connected to the valve body (142) and the variable pressure chamber (11).

4. The wearable breast pump according to claim 1, wherein the chamber cover plate (102) comprises an outer ring body (106) and a cover plate body (107); one end of the outer ring body (106) is connected to the housing (12) and the other end of the outer ring body (106) is connected to the cover plate body (107); the silicone suction cup (103) and the spacer (101) are placed on an inner circumference of the outer ring body (106) from bottom to top in turn, and a clamping groove (1080) is formed between the spacer (101) and the outer ring body (106) that fits with the silicone suction cup (103); an outer circumference of the outer ring body (106) is configured to connect to the cup (200); correspondingly, a bottom surface of the spacer (101) is provided with a limit ring (108) that is opposite to the outer ring body (106) to form the clamping groove (1080).

5. The wearable breast pump according to claim 1, wherein the flowing channel unit (300) further comprises a duckbill valve (33); the three-way valve (31) is formed thereon with an air vent (310), the liquid inlet (311) and a liquid outlet (312) respectively; the three-way valve (31) is communicated with the breast flange (32) through the air vent (310); the liquid outlet (312) of the three-way valve (31) is provided with the duckbill valve (33); and the liquid inlet (311) of the three-way valve (31) is communicated with the outside of the wearable breast pump.

6. The wearable breast pump according to claim 1, wherein the cup body (21) is formed thereon with an exhaust and liquid extraction port (205) that is positioned on an upper part of the cup body (21) and is adjacent to the host machine (100).

7. The wearable breast pump according to claim 1, wherein the first opening (201) of the cup body (21) is bent downward to form a clamping ring (206) that is provided thereon with a clamping recess (2060) fitting with the variable pressure chamber (11); correspondingly, an outer circumferential surface of the variable pressure chamber (11) is provided thereon with a clamping surface (109) fitting with the clamping recess (2060); and the outer circumferential surface of the variable pressure chamber (11) is further provided thereon with an upper abutting ring (110) positioned on an inner side of the clamping surface (109); correspondingly, the breast flange (32) is provided thereon with a fit lower abutting ring (34); and the upper abutting ring (110) and the lower abutting ring (34) can abut against each other.

8. The wearable breast pump according to claim 1, wherein one of the second opening (202) and the large-diameter end (203) is provided thereon with a hook plate (212), while the other one is formed thereon with a buckle groove (213); the hook plate (212) can be buckled into the buckle groove (213) to connect the cup body (21) and the silicone trumpet cover (22); the smaller-diameter end (204) is formed with an annular groove fitting with the flowing channel unit (300); one end of the flowing channel unit (300) is inserted into the annular groove, while the other end of the flowing channel unit (300) abuts against the cup body (21); and the three-way valve (31) in the flowing channel unit (300) is configured to connect to the silicone trumpet cover (22), hence the liquid inlet (311) of three-way valve (31) is constructed as an annular structure fitting with the annular groove.

\* \* \* \* \*